United States Patent [19]
Sarngadharan et al.

[11] Patent Number: 5,736,317
[45] Date of Patent: Apr. 7, 1998

[54] HUMAN T-CELL LINE INFECTED WITH HIV-2 WHICH SECRETES A PROTEIN CORRESPONDING TO NATIVE HIV-2 GP160 IN AN EXTRACELLULAR MEDIUM

[75] Inventors: Mangalasseril G. Sarngadharan, McLean, Va.; Vaniambadi S. Kalyanaraman, Germantown; Irene LaRue-Kalisz, Frederick, both of Md.

[73] Assignee: Akzo Nobel N.V., Arnhem, Netherlands

[21] Appl. No.: 402,481

[22] Filed: Mar. 7, 1995

[51] Int. Cl.$^6$ .................................. C12Q 1/70; C12N 7/00
[52] U.S. Cl. ............................ 435/5; 435/235.1; 435/325
[58] Field of Search ............................ 435/235.1, 325

[56] References Cited

U.S. PATENT DOCUMENTS 5,116,740  5/1992  Sarngadharan .................. 435/70.4
5,122,468  6/1992  Sarngadharan .................. 435/240

FOREIGN PATENT DOCUMENTS 37 12334 A  10/1988  Germany .

OTHER PUBLICATIONS

Getchell et al., "Continuous Production of a Cytopathic Human T-Lymphotropic Virus in a Permissive Neoplastic T-Cell Line," *Journal of Clinical Microbiology*, vol. 23, No. 4, pp. 737-742, Apr., 1986.

*Primary Examiner*—Ponnathapura Achutamurthy
*Assistant Examiner*—Hankyel T. Park
*Attorney, Agent, or Firm*—Gregory R. Muir; Mary E. Gormley

[57] ABSTRACT

A novel cell line chronically infected with HIV-2$_{NIHZ}$ virus secretes the precursor of the viral envelope proteins in extracellular medium. The cells grow well in serum-free medium which enables the concentration of the conditioned medium of the cells to be greatly increased (>100 fold). Such a concentration step is otherwise impossible to achieve if the cells are grown under conventional conditions using 10% fetal calf serum. A specific affinity procedure is provided to purify the gp160 protein from the concentrated conditioned medium of cultures of 100 liter batches using a mouse monoclonal antibody to the HIV-2 gp41 protein, which is a part of the gp160 protein. This purified HIV-2 gp160 reacts with high specificity and sensitivity with the anti viral antibodies of HIV-2 infected humans by several criteria such as i) ELISA, ii) western blot analysis, and iii) radioimmunoprecipitation of metabolically labeled gp160 from the same cell line. The purified HIV-2 gp160 from this cell line is therefore a diagnostic tool for the detection of HIV-2 infection in humans. In view of the predicted oligomeric property of gp160 and its close conformational similarity to the virion envelope, the purified gp160 can also be useful for the development of vaccine strategies against HIV-2 in humans.

5 Claims, 6 Drawing Sheets

1. HIV-2$_{NIHZ}$ gp160.
2. Molecular weight standards

1. HIV-2$_{NIHZ}$ gp160.
2. Molecular weight standards

Lane 1 Normal human serum; 2-14 HIV-2 antibody positive human sera.

Lanes 1-13 HIV-2 antibody positive human sera. Lane 14. Normal human serum.

| Sample # | Sample | $A_{450}$ | S/CO ratio |
|---|---|---|---|
| 1 | NHS-1 | 0.194 | - |
| 2 | NHS-2 | 0.182 | - |
| 3 | NHS-3 | 0.195 | - |
| 4 | G176 | >2 | >5 |
| 5 | G267 | >2 | >5 |
| 6 | 07810A | >2 | >5 |
| 7 | G183 | >2 | >5 |
| 8 | G157 | >2 | >5 |
| 9 | G272 | >2 | >5 |
| 10 | G199 | >2 | >5 |
| 11 | G160 | >2 | >5 |
| 12 | G7312 | >2 | >5 |

Samples 1, 2 and sera from uninfected humans and 4 through 12 are from HIV-2 infected individuals. The S/CO ratio was taken as the value representing twice the average $A_{450}$ of the uninfected individuals.

FIG. 6

HUMAN T-CELL LINE INFECTED WITH HIV-2 WHICH SECRETES A PROTEIN CORRESPONDING TO NATIVE HIV-2 GP160 IN AN EXTRACELLULAR MEDIUM

BACKGROUND OF THE INVENTION

The present invention relates to the production and characterization of Human Immunodeficiency Virus type 2 gp160. The virus has been demonstrated to have infected humans from a number of geographical areas of the world, and it has been further shown that HIV-2 infected individuals develop the disease characteristics similar to that of Acquired Immunodeficiency Syndrome (AIDS) caused by HIV-1. The course of disease progression in HIV-2 infected individuals is significantly slower than that of the pathogenesis caused by HIV-1.

HIV-2 is T-cell tropic just as HIV-1 is, and the CD4 antigen on the surface of T-cells acts as the virus receptor. The interaction of the viral envelope with the CD4 antigen initiates the virus infection process. The envelope glycoprotein of HIV-2 is synthesized in the virus infected cells as a precursor gp160, which is subsequently cleaved into the external envelope glycoprotein gp120 and the transmembrane gp41 protein before being packaged in the virus envelope. Unlike the gp41 in HIV-1, the transmembrane protein is present as intact gp41 or as truncated gp31 in the HIV-2 virions. Further, the HIV-2 virions with the truncated gp31 are highly infectious while the corresponding defective HIV-1 is non-infectious. This makes the biological and biochemical properties of the envelope proteins not readily comparable.

In view of their location, the envelope proteins gp120 and gp41 are the primary targets of immune response in HIV-2 infected humans. This is similar to the immune response to HIV-1 in HIV-1 infected individuals. However, the two viruses have less than 50% homology in their envelope proteins and hence it is difficult to extend the observations made in the HIV-1 system to the responses to HIV-2. For example, at least in animal model systems the primary target of the immune response is the V3 loop of the gp120 in the HIV-1 system, and this is true among very divergent HIV-1 isolates. On the other hand no such principal immune domain has been identified in the HIV-2 envelope protein. However, the one similarity between the two viruses is the extensive variability in the envelope glycoproteins among multiple isolates of both HIV-1 and HIV-2. This has limited the use of subunits of the gp120 or gp41 of HIV-2 for either diagnostic use or as candidate vaccines in humans.

The ability to obtain certain human T-cell lines chronically infected with defective forms of HIV-1, which secrete intact gp160, has been described in the U.S. Pat. Nos. 5,116,740 and 5,122,468. However, the ability to obtain such cell lines is not universally applicable to all variants of HIV-1. The case with HIV-2 is even more difficult to predict than that of HIV-1, as HIV-2 is far less cytopathic than HIV-1 and HIV-2 is still infectious with the truncated form of the gp31. Also, the development of either HIV-1 or HIV-2 infected cell lines secreting the envelope precursor protein gp160 is not generally applicable to all the diverse variants of these two viruses. Experience has demonstrated that each individual virus isolate is unique and requires selective handling and different manipulations of the culture system, which may still not yield success. The defining properties of the virus which ultimately lead to the secretory phenomenon are not yet clearly understood. For example, it has been repeatedly tried without success to develop cell lines secreting gp160 from a number of isolates, including another variant of HIV-2, HIV-2 $SBL_{6669}$. The development of the $6D5_{NIHZ}$ of the present invention took more than three years of developmental work with no clear chance of success, before a cell line was obtained which secreted HIV-2 gp160 in quantities suitable for large-scale isolation.

With respect to the HIV-1 group of viruses, during the last seven years of research and development, success has been reached only with the HIV-$1_{IIIB}$ isolate and the $6D5_{451}$ system set forth in U.S. Pat. Nos. 5,116,740 and 5,122,468. It has not been possible, after years of research, to develop a gp160 secreting cell line from most HIV isolates, including HIV-$1_{MN}$, HIV-$1_{CDC71}$, HIV-$1_{WOM}$, HIV-$1_{Z6}$, and HIV-$1_{Bal}$. It has also been attempted, but has repeatedly resulted in failure, to develop a cell line of $SIV_{mac251}$ infected cells which secrete $SIV_{mac251}$ gp160 ($SIV_{mac251}$ being clearly related to HIV-2 and having >70% homology in the envelope protein). In view of the uniqueness of each virus, and of each individual virus strain, as well as in view of the very few instances of being able to develop a cell line which secretes functionally intact gp160, the chance of success in developing any virus infected cell line which secretes gp160, and in particular the likelihood of developing a cell line which secretes HIV-2 gp160, functionally intact, is low.

Until the present invention, the gp160 of HIV-2 has been produced only by recombinant techniques. However, the glycosylation of the recombinant protein varies significantly, both qualitatively and quantitatively, from the native protein from HIV-2 infected cells. Because of this, there are differences in the conformation between gp160 from natural viral culture and the recombinant gp160. These have become critical issues for diagnostic and vaccine strategies against AIDS.

SUMMARY OF THE INVENTION

It is an object of the present invention to provide a unique clone of HUT78 cells which when chronically infected with HIV-$2_{NIHZ}$ isolate, releases functionally intact native viral glycoprotein gp160 into the extracellular medium.

Another object of the present invention is to provide a unique clone of the immortalized HIV-$2_{NIHZ}$ infected HUT78 cells grown in a serum-free medium under such conditions that the cell line releases native gp160 into the extracellular medium.

Yet another object of the present invention is to provide functionally intact purified HIV-2 gp160 in its native form.

A further object of the present invention is to provide the purified HIV-2 gp160 in its native form for the detection of antibodies to HIV-2 in infected humans by (1) ELISA; (2) Western blot; (3) radioimmunoprecipitation of metabolically labeled cells and the conditioned medium; and (4) by any other method employing antigen-antibody interaction.

Another object of the present invention is to provide the purified HIV-2 gp160 in its native form for use as an oligomeric protein and therefore as a vaccine reagent in humans.

3

(iii) three separate mouse monoclonal antibodies to HIV-2 gp41 (lanes 4, 5 and 6).

Figure 3:
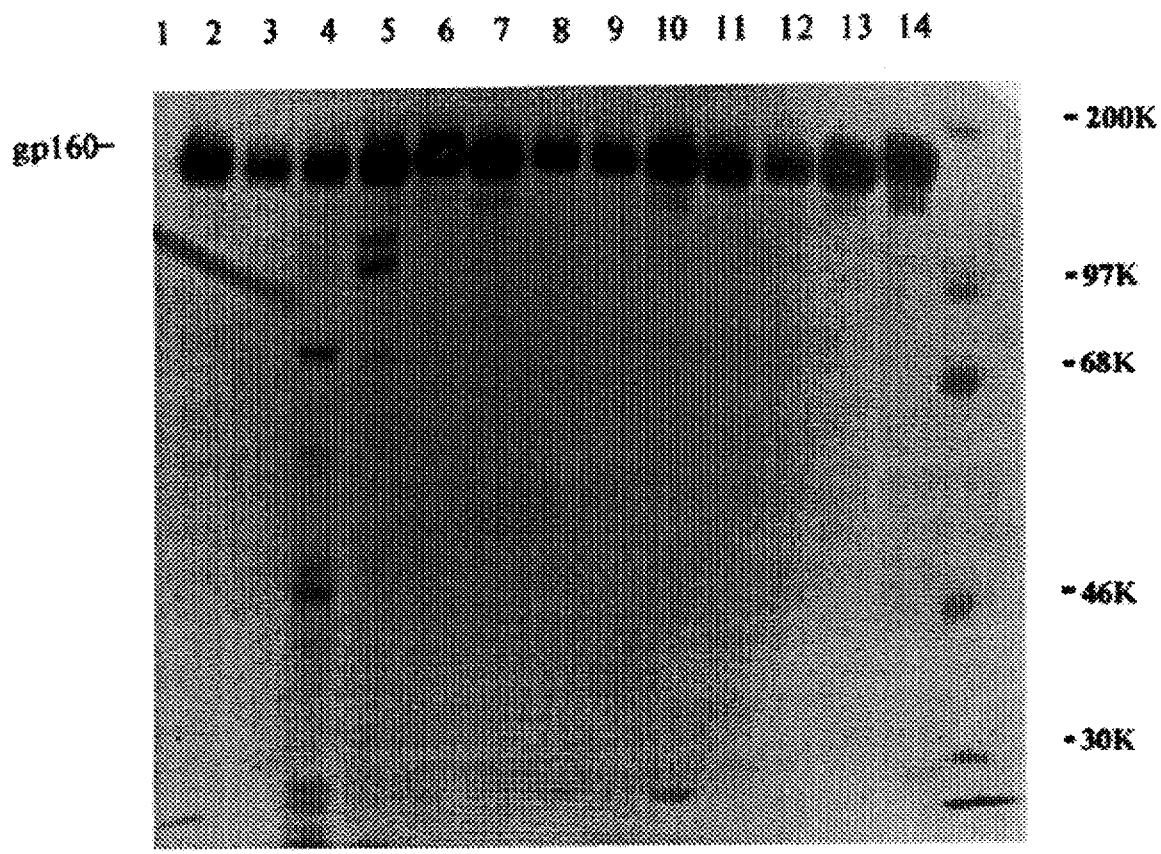

FIG. 3 shows the radioimmunoprecipitation of $^{35}$S-methionine labeled conditioned medium of 6D5$_{NIHZ}$ (clone 11) by thirteen different sera from HIV-2 infected humans.

Figure 4:
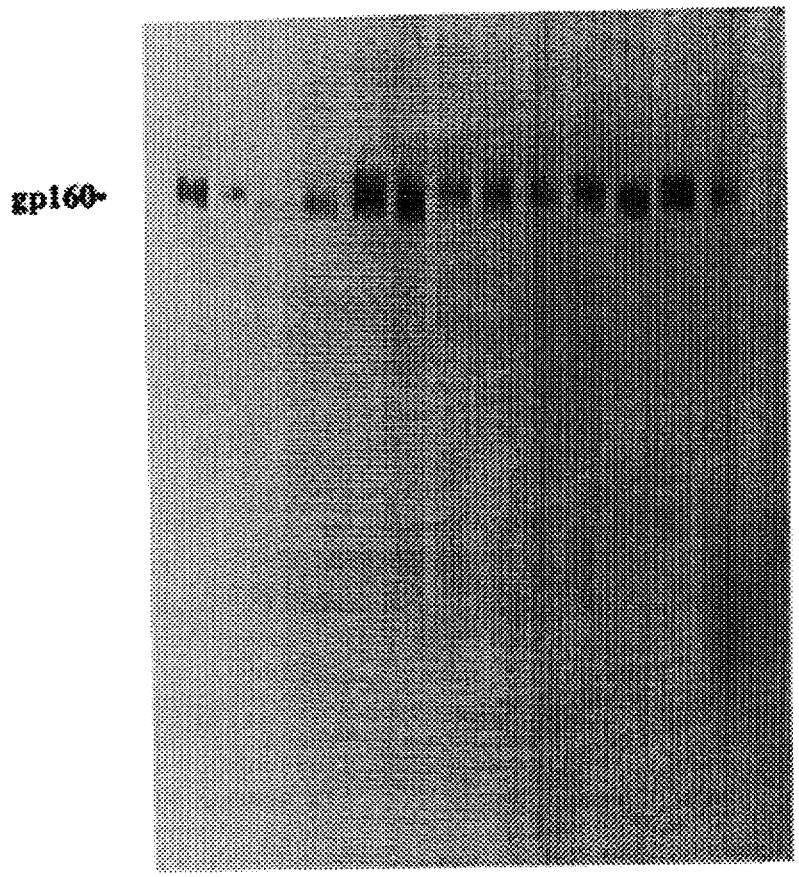

FIG. 4 shows the reactivity of HIV-2 antibody positive human sera in Western blot analysis with purified HIV-2 gp160 (same sera as in FIG. 3).

Figure 5:
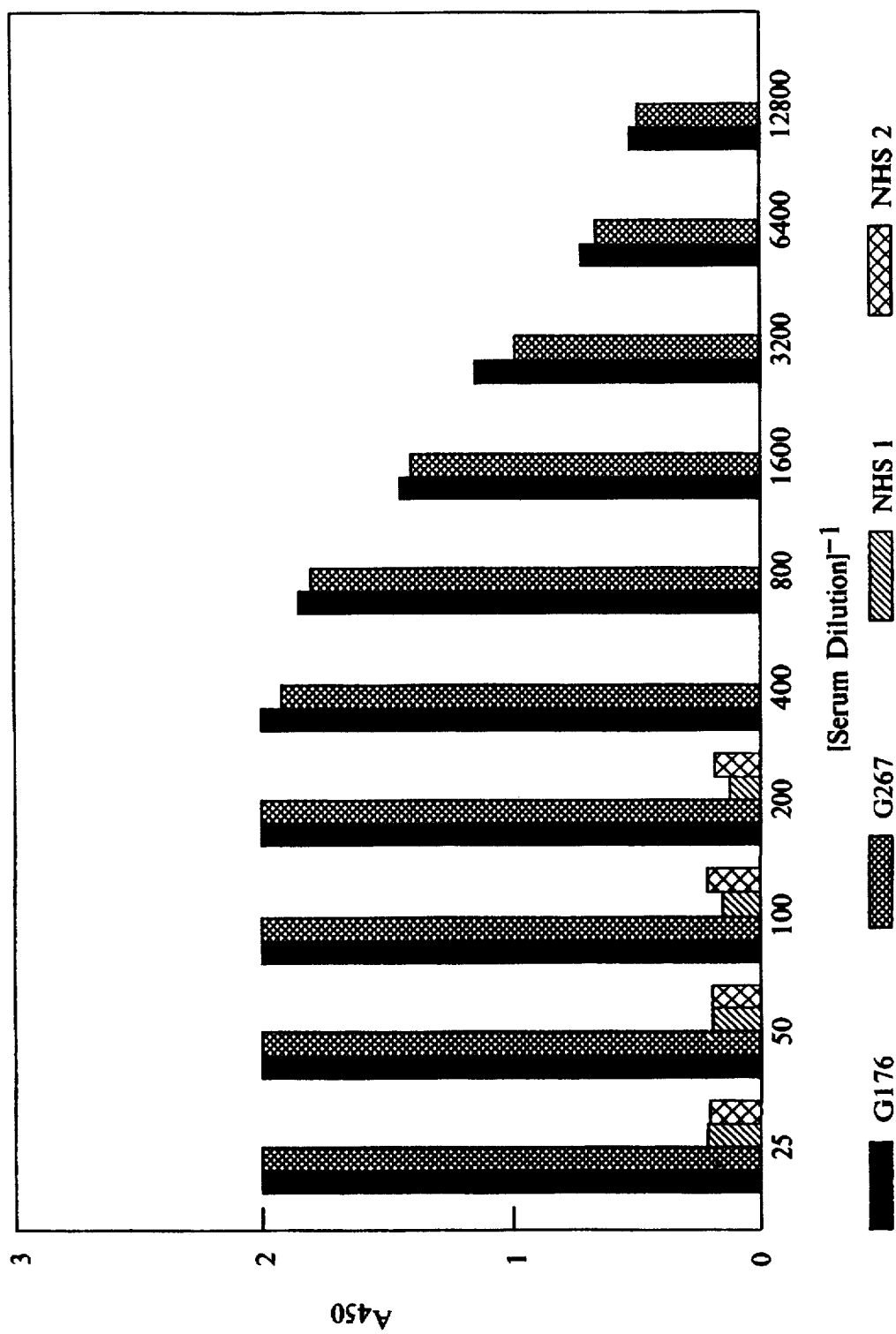

FIG. 5 shows the HIV-2 gp160 reaction with serial dilutions of two different sera from HIV-2 infected humans.

FIG. 6 shows the strong reactivity of HIV-2 antibody positive human sera in an ELISA of purified HIV-2 gp160.

DESCRIPTION OF THE PREFERRED EMBODIMENTS

A single cell clone of HUT78 cells has been infected with Human Immunodeficiency Virus Type I (HIV-1), whereby the infected cell line became a continuous producer of virus. Clone 6D5 is susceptible to chronic infection with HIV-1 as described in Getchell et al. (J. Clin. Microbiol. 23:737–742, 1986). In the present invention, the 6D5 clone is found to be highly susceptible to infection by a number of divergent HIV-2 isolates. In spite of the biological differences between HIV-1 and HIV-2, a method has now been found to infect the 6D5 cells with the HIV-2 isolate HIV-2$_{NIHZ}$ which cells secrete gp160 in the medium. The chronically infected cell line is designated as 6D5$_{NIHZ}$. A single cell clone of this cell line (clone 11) was isolated and was found to secrete high levels of HIV-2 gp160 in the medium. Importantly, the cloned cell line can be grown in a serum-free medium, such as serum-free HB104 medium commercially available from Irvine Scientific Co. (California). Growing the cells in serum-free medium is an essential step to concentrate and purify the HIV-2 gp160 from the conditioned medium of 6D5$_{NIHZ}$, clone 11 cells. Only when serum-free medium is used can glycoprotein gp160 be easily separated from other proteins in the media. gp160 cannot be easily separated from other media components when serum-containing media is used.

In the preferred embodiment, the HB104 serum supplement contains human transferrin, human insulin, human serum albumin and selenium as growth promoting factors. To obtain optimal growth and production of HIV-2 gp160, the 6D5$_{NIHZ}$ (clone 11) cells were grown for 3 to 4 generations in the serum-free medium. The presence of HIV-2 gp160 in the medium was detected by metabolic labelling of the cells with $^{35}$S-methionine overnight and radioimmunoprecipitation of the labeled proteins in the medium with HIV-2 antibody positive human serum.

Figure 1:
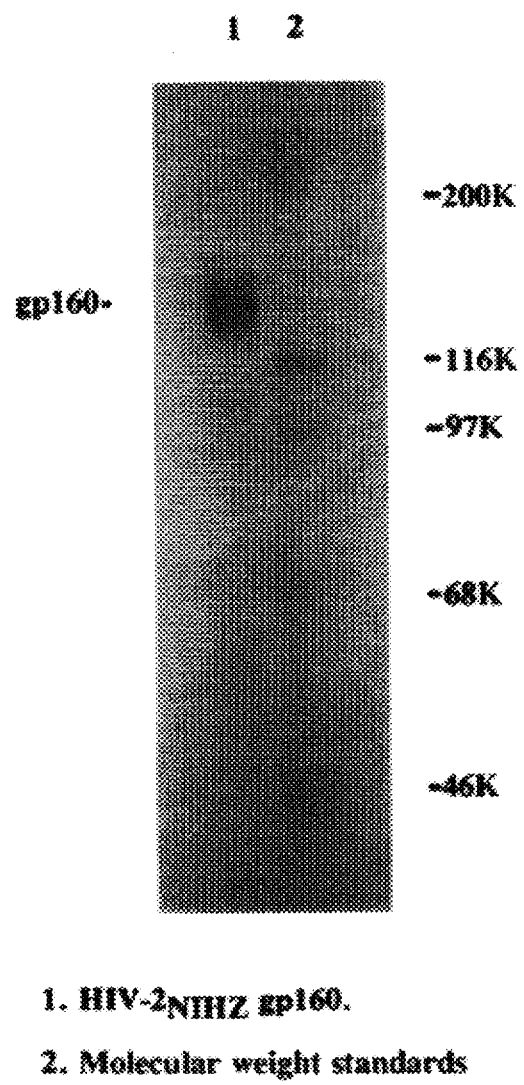
FIG. 1 shows the SDS-PAGE profile of affinity purified HIV-2 gp160.

The cell-free conditioned medium was used as the source of the HIV-2$_{NIHZ}$ gp160. Usually 50 to 100 liter batches of the cells are grown in the serum-free medium in roller bottles. Cells were removed from the medium and sodium phosphate pH 7.5, sodium chloride, Triton X-100, and PMSF were added to the conditioned medium to final concentrations of 20 mM, 400 mM, 0.5% and 0.1 mM respectively in order to inactivate infectious virus. After incubation at room temperature for one hour the inactivated medium was concentrated approximately 50 fold using a Pellicon Cassette fitted with a 10K molecular weight cut-off filter (Millipore Corporation). The HIV-2$_{NIHZ}$ gp160 was purified from the inactivated and concentrated conditioned medium by immunoaffinity chromatography using a mouse monoclonal antibody to HIV-2 gp41. The monoclonal antibody was developed by ABL using partially purified HIV-2$_{NIHZ}$ gp160. The purified immunoglobulin of the monoclonal antibody was coupled to CNBr activated Sepharose (purchased from Pharmacia) at a concentration of 5 mg per ml according to the manufacturer's recommendations. The concentrated conditioned medium of 6D5$_{NIHZ}$ (clone 11) cells was passed through a 50 ml column of the above antibody at 4° C. After washing the column with phosphate buffered saline and then saline, the bound proteins from the column were eluted with 100 mM sodium carbonate containing 0.1 mM PMSF. The elution of the protein from the column was monitored by absorbance measurement at 280 nm using a LKB UVICORD connected to a recorder. The eluted protein was neutralized using 2N HCl and sodium phosphate pH 7.5 was added to a final concentration of 10 mM. This fraction contained HIV-2$_{NIHZ}$ gp160 along with human serum albumin (HSA) as a contaminant. To remove HSA, the sample was passed through a column of goat antibody to HSA (purchased from Cappel labs) coupled to Sepharose (5 mg per ml of Sepharose). The unbound fraction was concentrated to 10 to 20 ml and stored in suitable aliquots at –70° C. FIG. 1 shows the SDS-PAGE profile of purified HIV-2$_{NIHZ}$ gp160. The purified protein was run in 7.5% SDS gels, stained with Comassie Blue, destained and photographed.

A deposit of 6D5$_{NIHZ}$ (clone 11) cells described herein was made under the requirements of the Budapest Treaty with the American Type Culture Collection (ATCC), 12301 Parklawn Drive, Rockville, Md. 20852, USA, on Jan. 25, 1995, ATCC designation CRL-11826.

EXAMPLES

Example 1

Figure 2:
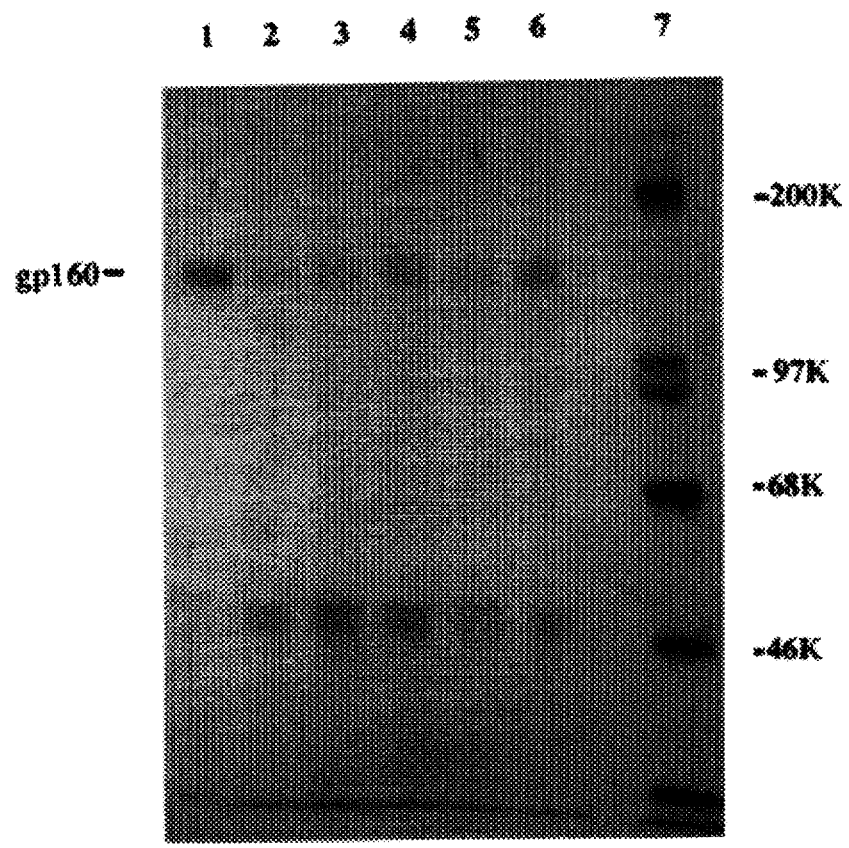
FIG. 2 shows SDS-PAGE profile of the $^{35}$S-methionine labeled protein of $6D5_{NIHZ}$ (clone 11) cells and the conditioned medium, immunoprecipitated with (i) HIV-2 antibody positive human serum (lane 1); (ii) two separate mouse monoclonal antibodies to HIV-2 gp120 (lanes 2 and 3)

Five million 6D5$_{NIHZ}$ (clone 11) cells in 5 ml of methionine-free RPMI 1640 medium containing 2% dialyzed fetal calf serum and 100 μC per ml of $^{35}$S-methionine (NEN DuPont) were incubated at 37° C. for 15 hours. The cells were removed by centrifugation and an equal volume of 2X PBS-TD buffer (2X PBS containing 2% Triton X-100, 1M sodium deoxycholate and 0.1 mM PMSF) was added. To 1 ml of this mixture was added either 10 μl HIV-2 antibody positive human serum or 50 μg mouse monoclonal antibody to HIV-2 gp120 or gp41. In addition 200 μl of 10% Protein-A Sepharose (the Protein A Sepharose was presaturated with rabbit antibody to mouse IgG in the case of monoclonal antibodies) was also added to the samples. The mixture was incubated for one hour at room temperature. The samples were centrifuged for 2 minutes at 10,000 rpm in an Eppendorf centrifuge and the pellet was washed three times with PBS-TD buffer. The Sepharose pellet was boiled for 2 minutes with buffer containing 2% SDS, 2% β-mercaptoethanol, 50 mM Tris-HCl pH 6.8 and 20% glycerol. The solubilized labeled proteins were separated in 7.5% SDS-PAGE gels, treated with Amplify (Amersham) dried and exposed to X Ray film. FIG. 2 shows that the medium contained an approximately 140 kD protein band immunoprecipitated by all the three above antibodies demonstrating that it represented the truncated form of HIV-2 gp160.

Example 2

The viral proteins in the extracellular medium of 6D5$_{NIHZ}$ (clone 11) cells labeled with $^{35}$S-methionine were immunoprecipitated with 12 different HIV-2 antibody positive human sera (obtained from Serologicals Inc.) as described above. The labeled medium was preincubated with 10 μl of HIV-2 antibody-negative normal human serum and 200 μl of 10% Protein-A Sepharose for one hour at room temperature and centrifuged. The clarified supernatant was reactive with specific antibody positive sera. As shown in FIG. 3 all the HIV-2 antibody positive human sera strongly precipitated the gp160 protein from the labeled conditioned media.

Example 3

In Example 2, the labeled gp160 protein secreted by the $6D5_{NIHZ}$ (clone 11) cells was immunoprecipitated specifically and with high sensitivity by all the HIV-2 antibody positive human sera. We further showed that all the HIV-2 antibody positive human sera also reacted with high specificity in Immunoblots with purified HIV-2 gp160 shown in FIG. 1. For this purpose the purified HIV-2 gp160 was separated in 7.5% SDS-PAGE gels and transferred to nitrocellulose by electroblotting. The nitrocellulose was blocked with non-fat dry milk and cut into 4 mm strips. The strips were treated with 20 µl of the HIV-2 antibody positive human sera or negative control sera during 2 hour incubation in 5 ml of buffer (10 mM Tris HCl pH 7.5, 10 30mM NaCl and 0.05% Tween 20). The strips were washed and the bound antibodies were visualized using alkaline phosphatase conjugated goat anti human IgG. As shown in FIG. 4 all the HIV-2 antibody-positive sera, but not the negative control serum, reacted with purified HIV-2 gp160

Example 4

One of the convenient methods used in the mass detection of antibodies against specific pathogen in human sera is by ELISA. Therefore, the ability of purified HIV-2 gp160 from $6D5_{NIHZ}$ (clone 11) cells to detect virus specific antibodies in this format was tested. For this purpose 96 well ELISA plates were coated with 100 ng per well of purified gp160 and the wells were treated with 100 µl of 1:25 diluted human sera. The bound antibodies were detected with peroxidase conjugated second antibody by standard techniques. The absorbance in the wells at 450 nm was measured in an ELISA reader. As shown in FIG. 6 the purified HIV-2 gp160 was detected specifically and with high sensitivity as measured by the sample to cutoff ratios.

FIG. 5 shows the sensitivity of detection of antibodies to HIV-2 in two different human sera. For this purpose two fold serial dilutions of the sera were reacted with HIV-2 gp160 in the ELISA plate and the absorbance was measured at 450 nm. As is evident from the figure, the purified HIV-2 gp160 reacts with high sensitivity with these sera and probably reacts with a variety of epitopes in the purified protein.

We claim:

1. A HUT78 T-cell line infected with HIV-$2_{NIHZ}$ which secretes a protein corresponding to native HIV-2 gp 160.

2. A cell line according to claim 1, wherein said cell line is $6D5_{NIHZ}$, ATCC designation CRL-11826.

3. $6D5_{NIHZ}$ cells selected from ATCC designation CRL-11826 in a serum-free medium.

4. A method for the production of a protein corresponding to native HIV-2 gp160 comprising: infecting cells from a HUT78 T-cell line with HIV-$2_{NIHZ}$; selecting infected HUT78 cells that produce a protein corresponding to native gp160; incubating said gp160 producing cell line in serum-free medium under conditions that promote cell growth; and isolating a protein corresponding to native gp160 from said medium.

5. In a process for the production of envelope proteins from HIV-2 wherein a T-cell line is infected with said HIV-2, incubated in a medium under conditions that promote cell growth, and glycoproteins are secreted into said medium, the improvement which comprises: incubating cells from a gp160 producing $6D5_{NIHZ}$ infected T-cell line in serum-free medium, and isolating from said medium an approximately 140 kD protein which corresponds to native HIV-2 envelope glycoprotein gp160.

* * * * *